United States Patent
Tang et al.

(10) Patent No.: US 12,268,657 B2
(45) Date of Patent: Apr. 8, 2025

(54) COENZYME Q10 COMPOSITION, AND PREPARATION METHOD AND APPLICATION THEREOF IN CARDIO-PROTECTION

(71) Applicant: Guangdong Runhe Biotechnology Co., Ltd, Guangzhou (CN)

(72) Inventors: Linzhi Tang, Guangzhou (CN); Xinbao Mo, Guangzhou (CN); Jifu Zhang, Guangzhou (CN); Dong Si, Guangzhou (CN); Xianbiao Yang, Guangzhou (CN); Haoxin Yuan, Guangzhou (CN); Faquan Yang, Guangzhou (CN); Simin Lv, Guangzhou (CN)

(73) Assignee: Guangdong Runhe Biotechnology Co., Ltd, Guangzhou (CN)

( * ) Notice: Subject to any disclaimer, the term of this patent is extended or adjusted under 35 U.S.C. 154(b) by 0 days.

(21) Appl. No.: 18/926,566

(22) Filed: Oct. 25, 2024

(65) Prior Publication Data

US 2025/0041242 A1    Feb. 6, 2025

(30) Foreign Application Priority Data

Oct. 26, 2023    (CN) .......................... 202311401630.5

(51) Int. Cl.
| | | |
|---|---|---|
| *A61K 31/122* | (2006.01) | |
| *A61K 9/70* | (2006.01) | |
| *A61K 47/34* | (2017.01) | |
| *A61K 47/36* | (2006.01) | |
| *A61P 9/10* | (2006.01) | |

(52) U.S. Cl.
CPC .......... *A61K 31/122* (2013.01); *A61K 9/7007* (2013.01); *A61K 47/34* (2013.01); *A61K 47/36* (2013.01); *A61P 9/10* (2018.01)

(58) Field of Classification Search
CPC ........ A61K 31/122; A61K 9/7007; A61P 9/10
See application file for complete search history.

(56) References Cited

U.S. PATENT DOCUMENTS

2012/0021059 A1    1/2012    Takano

FOREIGN PATENT DOCUMENTS

| CN | 101596177 A | 12/2009 |
|---|---|---|
| CN | 106727441 A | 5/2017 |
| CN | 111579672 A | 8/2020 |
| CN | 114699512 A | 7/2022 |
| CN | 116869971 A | 10/2023 |

*Primary Examiner* — Robert A Wax
*Assistant Examiner* — William Craigo

(57) ABSTRACT

A coenzyme $Q_{10}$ slow-release drug includes an isolation layer and a drug layer, where the drug layer is composed of coenzyme $Q_{10}$ and a pharmaceutically acceptable carrier; the isolation layer is composed of a degradable gel; a diameter of the drug layer is not larger than that of the isolation layer. The coenzyme $Q_{10}$ slow-release drug is prepared as follows. (S1) The degradable gel is laid on a mold for casting into a film to form the isolation layer. (S2) Coenzyme $Q_{10}$ and the pharmaceutically acceptable carrier are mixed and laid on the mold in step (S1) for casting to form the drug layer on the isolation layer. (S3) Steps (S1) and (S2) are repeated, and then edges of adjacent controlled-release layers are bonded to obtain the coenzyme $Q_{10}$ slow-release drug.

3 Claims, No Drawings

COENZYME Q10 COMPOSITION, AND PREPARATION METHOD AND APPLICATION THEREOF IN CARDIO-PROTECTION

CROSS-REFERENCE TO RELATED APPLICATIONS

This application claims the benefit of priority from Chinese Patent Application No. 202311401630.5, filed on Oct. 26, 2023. The content of the aforementioned application, including any intervening amendments thereto, is incorporated herein by reference in its entirety.

TECHNICAL FIELD

This application relates to cardiac therapeutics, and more specifically to a coenzyme $Q_{10}$ composition, and a preparation method and an application thereof in the cardio-protection.

BACKGROUND

Ubiquinone (UQ), also known as Coenzyme Q, is a natural fat-soluble quinone compound. The ubiquinone molecule contains a side chain connected to the parent nucleus benzoquinone, which consists of multiple polyisoprene units. The length of the side chain varies depending on the source of the ubiquinone, which is determined by the reaction catalyzed by polyisoprene pyrophosphate synthase, typically contains 6-10 of polyisoprene units (n). In mammals and humans, n=10, hence, the ubiquinone is called Coenzyme $Q_{10}$ ($CoQ_{10}$).

$CoQ_{10}$ has the functions of improving human immunity, offering an antioxidant effect, delaying aging and enhancing the human vitality, which is the most effective antioxidant ingredient for preventing the formation of atherosclerosis, and is widely used in the prevention and control of cardiovascular system diseases, such as myocardial infarction, thrombosis, heart failure, angina pectoris, and heartbeat abnormalities. Meanwhile, it can lower blood pressure and blood lipids, promote the treatment and recovery after cardiac surgery, protect athletes from cardiac malfunction caused by myocardial overburdening, and effectively improve myocardial weakness and poor cardiac function. As such, it has been widely used as a natural antioxidant and a free radical scavenger in pharmaceuticals and health care products, cosmetic products and food additives at home and abroad. Particularly, it has been recommended as the most effective heart-care product in Europe, America and Japan.

However, the therapeutic effect of the existing clinical coenzyme $Q_{10}$ drugs still needs to be further enhanced, especially in how to achieve the long-term effective protection of patients' cardiac function and avoid the extra burden caused by myocardial infarction.

SUMMARY

An objective of the present disclosure is to provide a coenzyme $Q_{10}$ composition, and a preparation method and an application thereof in the cardio-protection to solve the above technical problems in the prior art. It has been verified that the coenzyme $Q_{10}$ slow-release medicine of the present disclosure can effectively reduce the infarction size, and has good protective and repairing effects on the myocardial ischemic injury.

The technical solutions of the present disclosure are as follows.

In a first aspect, this application provides a coenzyme $Q_{10}$ slow-release drug, comprising:
an isolation layer; and
a drug layer;
wherein the coenzyme $Q_{10}$ slow-release drug is prepared by layer-by-layer stacking the isolation layer and the drug layer; the drug layer is composed of coenzyme $Q_{10}$ and a pharmaceutically acceptable carrier; the isolation layer is composed of a degradable gel; and a diameter of the drug layer is not larger than that of the isolation layer.

Preferably, the pharmaceutically acceptable carrier is selected from the group consisting of collagen, gelatin, hyaluronic acid, alginate and salts thereof, and a combination thereof.

Preferably, the degradable gel is selected from the group consisting of polyethylene glycol, polyvinyl alcohol, chitosan, poly (L-lactic acid), polylactic acid-hydroxyacetic acid copolymer, and a combination thereof.

Preferably, the drug layer contains 50-80% by weight of the coenzyme $Q_{10}$.

Preferably, the pharmaceutically acceptable carrier is composed of hyaluronic acid and sodium alginate.

Preferably, a ratio of the hyaluronic acid to the sodium alginate is 3:4-8.

Preferably, the degradable gel is composed of chitosan and polylactic acid-hydroxyacetic acid copolymer.

Preferably, a ratio of the chitosan to the polylactic acid-hydroxyacetic acid copolymer is 5:1-4.

In a second aspect, this application provides a method of preparing the aforementioned coenzyme $Q_{10}$ slow-release drug, comprising:
(S1) laying the degradable gel on a mold followed by casting to form the isolation layer;
(S2) mixing the coenzyme $Q_{10}$ with the pharmaceutically acceptable carrier followed by spreading on the mold in step (S1) and casting to form the drug layer on the isolation layer; and
(S3) repeating steps (S1) and (S2); and bonding edges of adjacent isolation layers to obtain the coenzyme $Q_{10}$ slow-release drug.

In a third aspect, this application provides a method for protecting heart in a subject in need thereof, comprising:
administering a therapeutically effective amount of the aforementioned coenzyme $Q_{10}$ slow-release drug cardioprotective drug to the subject.

The beneficial effects of the present disclosure are as follows.

The present disclosure provides a controllable slow-release coenzyme $Q_{10}$ drug for the first time, which has a multilayer structure prepared through layer-by-layer alternate stacking of a degradable isolation layer and a drug layer. Compared with the traditional slow-release drug, the slow-release drug of the present disclosure has a simpler and more efficient preparation process, and shows an excellent slow-release effect. It can effectively control the in-vivo release rate of coenzyme $Q_{10}$, thereby offering a more efficient therapeutic effect.

DETAILED DESCRIPTION OF EMBODIMENTS

The present disclosure will be described in further detail below with reference to specific embodiments to enable one of ordinary skill in the art to understand the present disclosure clearer.

Example 1

Provided herein was a coenzyme $Q_{10}$ slow-release drug, which included an isolation layer and a drug layer. The coenzyme $Q_{10}$ slow-release drug was prepared by layer-by-layer stacking of the isolation layer and the drug layer, where the drug layer was composed of coenzyme $Q_{10}$ and a pharmaceutically acceptable carrier; the isolation layer was composed of a degradable gel; and a diameter of the drug layer was not larger than that of the isolation layer.

The pharmaceutically acceptable carrier was a mixture of collagen and gelatin in a weight ratio of 3:4-8.

The degradable gel was a mixture of chitosan and a polylactic acid-hydroxyacetic acid copolymer in a weight ratio of 5:1-4.

The coenzyme $Q_{10}$ slow-release drug was prepared through the following steps.

(S1) The degradable gel was laid on a mold for casting into a film to form the isolation layer.

(S2) Coenzyme $Q_{10}$ and the pharmaceutically acceptable carrier were mixed and laid on the isolation layer for casting to form the drug layer.

(S3) Steps (S1) and (S2) were repeated several times. Edges of adjacent isolation layers were bonded to obtain the coenzyme $Q_{10}$ slow-release drug.

Example 2

Provided herein was a coenzyme $Q_{10}$ slow-release drug, which included an isolation layer and a drug layer. The coenzyme $Q_{10}$ slow-release drug was prepared by layer-by-layer stacking of the isolation layer and the drug layer, where the drug layer was composed of coenzyme $Q_{10}$ and a pharmaceutically acceptable carrier; the isolation layer was composed of a degradable gel; and a diameter of the drug layer was not larger than that of the isolation layer.

The pharmaceutically acceptable carrier was a mixture of gelatin and hyaluronic acid in a weight ratio of 3:4-8.

The degradable gel was a mixture of chitosan and poly-L-lactic acid in a weight ratio of 5:1-4.

The coenzyme $Q_{10}$ slow-release drug was prepared through the following steps.

(S1) The degradable gel was laid on a mold for casting into a film to form an isolation layer.

(S2) Coenzyme $Q_{10}$ and the pharmaceutically acceptable carrier were mixed and laid on the isolation layer for casting to form the drug layer.

(S3) Steps (S1) and (S2) were repeated several times. Edges of adjacent isolation layers were bonded to obtain the coenzyme $Q_{10}$ slow-release drug.

Example 3

Provided herein was a coenzyme $Q_{10}$ slow-release drug, which included an isolation layer and a drug layer. The coenzyme $Q_{10}$ slow-release drug was prepared by layer-by-layer stacking of the isolation layer and the drug layer, where the drug layer was composed of coenzyme $Q_{10}$ and a pharmaceutically acceptable carrier; the isolation layer was composed of a degradable gel; and a diameter of the drug layer was not larger than that of the isolation layer.

The pharmaceutically acceptable carrier was a mixture of hyaluronic acid and alginic acid in a weight ratio of 3:4-8.

The degradable gel was a mixture of chitosan and poly-lactic-glycolic acid copolymer in a weight ratio of 5:1-4.

The coenzyme $Q_{10}$ slow-release drug was prepared through the following steps.

(S1) The degradable gel was laid on a mold for casting into a film to form an isolation layer.

(S2) Coenzyme $Q_{10}$ and the pharmaceutically acceptable carrier were mixed and laid on the isolation layer for casting to form the drug layer.

(S3) Steps (S1) and (S2) were repeated several times. Edges of adjacent isolation layers were bonded to obtain the coenzyme $Q_{10}$ slow-release drug.

Example 4

The slow-release characteristic of the coenzyme $Q_{10}$ slow-release drugs prepared by the present disclosure was evaluated as follows. Coenzyme $Q_{10}$ slow-release drugs (10 mg) prepared in Examples 1-3 were respectively dissolved in 10 mL of PBS solution, and shaken at 150 r/min and 37° C. in a constant-temperature shaker. Samples were taken at intervals, and analyzed by liquid chromatography for the released amount of coenzyme $Q_{10}$. The results showed that at day 1, the release rates of the coenzyme $Q_{10}$ slow-release drugs of Examples 1-3 reached 10%, 12% and 15%, respectively. The coenzyme $Q_{10}$ was continuously released at a relatively low rate, and on day 10, the release rates of the slow-release drugs of Examples 1-3 reached 95±0.8%, 96±1.2% and 98±2.6%, respectively, indicating that the coenzyme $Q_{10}$ slow-release drug prepared by the present disclosure had a good slow-release effect.

Example 5

The protective effect of the drug prepared in the present disclosure on the myocardial ischemia was demonstrated with the coenzyme $Q_{10}$ slow-release drug prepared in Example 3 as an example. Specifically, several SD rats weighing about 200 g were selected to prepare myocardial ischemia rat models by a coronary artery clamping method. The successful-established model rats were uniformly divided into a blank group, a control group, and a treatment group, with 8 rats in each group. The blank group was not treated with any drug during the observation period, the control group was administered with 0.2 mg/kg of coenzyme $Q_{10}$ per day for one week, and the treatment group was administered with 0.2 mg/kg of the coenzyme $Q_{10}$ slow-release drug per day for one week. After the one-week administration, the myocardial infarction area, and superoxide dismutase (SOD) and malondialdehyde (MDA) content in the serum of the rats after artery ligation were recorded, and the results were shown in the table below. It was found that the coenzyme $Q_{10}$ slow-release drug of the present disclosure can significantly reduce the myocardial infarction area, and had a good protection and repair effect on the myocardial ischemic injury. Moreover, after treatment with the slow-release drug, the activity of SOD was improved, and the generation of MDA was inhibited, which was favorable to reducing the occurrence of infarction.

TABLE 1

Protective effect of a coenzyme $Q_{10}$ slow-release drug on myocardial ischemia

| Groups | Myocardial infarction area (%) | SOD (NU/mL) | MDA (nmol/mL) |
| --- | --- | --- | --- |
| Blank group | 18.96 ± 1.52 | 195.45 ± 10.25 | 8.93 ± 0.98 |
| Control group | 14.69 ± 1.14 | 220.34 ± 8.56 | 6.57 ± 0.68 |
| Treatment group | 5.68 ± 1.65 | 297.42 ± 12.20 | 2.36 ± 0.64 |

It should be noted that the above embodiments are merely illustrative of the technical solutions of the present disclosure, rather than limiting the present disclosure Described above are some preferred embodiments, which are not intended to limit the scope of the present disclosure. Any modifications, equivalent replacements, and improvements made within the spirit and principles of the present disclosure shall be included in the scope of the present disclosure defined by the appended claims.

What is claimed is:

1. A coenzyme $Q_{10}$ slow-release drug, comprising:
an isolation layer; and
a drug layer;
wherein the coenzyme $Q_{10}$ slow-release drug is prepared by layer-by-layer stacking of the isolation layer and the drug layer; the drug layer comprises coenzyme $Q_{10}$ and a pharmaceutically acceptable carrier; the isolation layer is composed of a degradable gel; a diameter of the drug layer is not larger than that of the isolation layer; the pharmaceutically acceptable carrier is a mixture of hyaluronic acid and alginate in a weight ratio of 3:4-8; and the degradable gel is a mixture of chitosan and a polylactic acid-hydroxyacetic acid copolymer in a weight ratio of 5:1-4; and
the coenzyme $Q_{10}$ slow-release drug is prepared through steps of:

(S1) laying the degradable gel on a mold followed by casting to form the isolation layer;

(S2) mixing the coenzyme $Q_{10}$ with the pharmaceutically acceptable carrier followed by spreading on the mold in step (S1) and casting to form the drug layer on the isolation layer; and (S3) repeating steps (S1) and (S2); and bonding edges of adjacent isolation layers to obtain the coenzyme $Q_{10}$ slow-release drug.

2. A method of preparing the coenzyme $Q_{10}$ slow-release drug of claim 1, comprising:

(S1) laying the degradable gel on a mold followed by casting to form the isolation layer;

(S2) mixing the coenzyme $Q_{10}$ with the pharmaceutically acceptable carrier followed by spreading on the mold in step (S1) and casting to form the drug layer on the isolation layer; and (S3) repeating steps (S1) and (S2); and bonding edges of adjacent isolation layers to obtain the coenzyme $Q_{10}$ slow-release drug.

3. Use of the coenzyme $Q_{10}$ slow-release drug of claim 1 for protecting heart in a subject in need thereof, comprising:
administering a therapeutically effective amount of the coenzyme $Q_{10}$ slow-release drug to the subject.

* * * * *